United States Patent [19]

Wiersma et al.

[11] Patent Number: 5,698,191
[45] Date of Patent: Dec. 16, 1997

US005698191A

[54] NON-LETHAL BIO-REPELLENT COMPOSITIONS

[75] Inventors: Charles Wiersma; Jack Wiersma, both of Tequesta, Fla.

[73] Assignee: Nouveau Technologies, Inc., Tequesta, Fla.

[21] Appl. No.: 594,341

[22] Filed: Jan. 30, 1996

[51] Int. Cl.$^6$ .................... C08L 93/00; A01N 25/10
[52] U.S. Cl. ............ 424/78.09; 424/413; 424/195.1; 523/12.2; 106/17
[58] Field of Search ................... 424/405, 409, 424/78.09

[56] References Cited

U.S. PATENT DOCUMENTS

| | | |
|---|---|---|
| 5,017,562 | 5/1991 | Holmes et al. . |
| 5,226,380 | 7/1993 | Fischer . |
| 5,240,708 | 8/1993 | Plummer et al. . |
| 5,290,557 | 3/1994 | Mason et al. . |
| 5,397,385 | 3/1995 | Watts . |
| 5,466,459 | 11/1995 | Wilson ............... 424/405 |

OTHER PUBLICATIONS

JP 57/188509 Derwent Abstract, Nov. 1982.

JP 3152169-A Jun. 1991 Derwent Abstract.

Encyclopedia of Chemical Technology, Third Edition, Suppl. Volume (Carlson), pp. 797–805, "Repellents".

*Primary Examiner*—Peter F. Kulkosy
*Attorney, Agent, or Firm*—McHale & Slavin

[57] ABSTRACT

Disclosed is a non-lethal bio-repellent composition comprising a carrier, a bio-repellent amount of capsicum oleoresin, and an amount of a saponin sufficient to enhance the effectiveness of the capsicum oleoresin, whose bio-repellent effectiveness is greater than that of either capsicum oleoresin or saponin in absence of the other. Water, fatty acid glycerides, and various polymer emulsions can be used as carriers. The compositions are effective in preventing or minimizing the occupation and soiling of various surfaces by unwanted vertebrate animals such a birds and rodents and invertebrate animals such as insects, molluscs, and crustaceans.

21 Claims, No Drawings

NON-LETHAL BIO-REPELLENT COMPOSITIONS

BACKGROUND OF THE INVENTION

1. Field of the Invention

This invention relates to new and improved non-lethal and environment friendly bio-repellent compositions effective in preventing or minimizing for extended periods of time the occupation, damaging, or soiling of various surfaces by unwanted vertebrate animals such as birds, amphibians and rodents and invertebrate animals such as insects, molluscs, and crustaceans.

2. Description of the Related Art

Attempts to defeat, deter, or at least discourage unwanted animal incursions into zones of human residence and endeavor are as ancient as the scarecrow. It is sufficient to mention the damage and economic loss caused by rats gnawing electrical cables, by termites in homes constructed of wood, by birds occupying and soiling airport runways, docks, and recreation areas, and by barnacles and other marine life attaching to boat hulls, to bring to mind the host of situations in which animal activity generates objectionable effects ranging from nuisances to acute danger.

One widely practiced attempt to solve these problems has involved the use of materials toxic to the unwanted animals with as little toxic effect on humans and desirable animal life as possible. For example, anti-fouling paints for ship bottoms were traditionally formulated with copper and mercury oxides, poisonous to marine growth, using binders which permit gradual breakdown of the film and release of poison. A more recent development entails the addition to marine paints of tributyltin compounds such as tributyltin oxide, a liquid miscible with non-aqueous paint vehicles, and tributyltin fluoride, a solid with very low solubility in water. In spite of their low water solubility, these agents still leached from paints at rates deemed excessive both from the aspect of limited durability and possible hazard to humans and desirable marine organisms such as oysters. Research toward the goal of finding effective biocides that are less hazardous has led to the development of acrylic polymers in which tributyltin is chemically tied to the polymer molecule, as disclosed, for example, in Milne et al. U.S. Pat. No. 4,021,392. Nevertheless, a 1988 act of the United States Congress and similar actions in European countries has banned the use of any tributyltin compound in paints applied to vessels less than 25 meters long, thus eliminating the use of tributyltin on recreational boats.

There have also been numerous attempts to control unwanted animal life without killing through the use of a variety of substances as repellents. There is not always a clear dividing line between pesticides and repellents, with some agents exhibiting both kinds of effectiveness depending on concentrations and the kind of animal. For example, according to D. Carlson writing in Encyclopedia of Chemical Technology, third edition, Supplement volume, the insecticide diazinon (diethyl 2-isopropyl-6-methylpyrimidin-4-yl phosphorothioate) has been reported to be the pesticide of choice for modern cockroach control since cockroaches can be seen avoiding treated surfaces. The insecticide aldicarb (2-methyl-2-methylthiopropionaldoxime N-methylurethane) has been used as a bird repellent in the protection of sugar beets. Thiram (N,N,N'N'-tetramethylthiuram disulfide) has been used as active ingredient in a number of products offered as repellents for deer, rabbits, and field mice; other reportedly active ingredients of deer repellents included in the products tabulated in Carlson's article (at page 802) include putrescent whole egg solids, bone tar oil, zinc dimethyldithiocarbamate-cyclohexylamine complex, ammonium soaps of higher fatty acids, capsaicin (trans-8-methyl N-vanillyl-6-nonenoamide), and t-butyl N,N'dimethyl dithiocarbamate. Carlson, however, defines a repellent as a compound or combination of compounds that, when added to a food source (emphasis added) acts through the taste system to produce a marked decrease in the utilization of that food by the target species. Hence there is no suggestion that repellents as listed by Carlson would have any utility against species, such as water birds or barnacles, that while feeding elsewhere objectionably attach to or soil a surface of concern.

Watts U.S. Pat. No. 5,397,385 discloses a marine anti-fouling coating utilizing capsaicin as anti-fouling agent, mixed with a coating material such as a corrosion resistant epoxy resin which is then mixed with a hardening catalyst and applied to the surface to be treated. Finely divided inert particles may be added to impart additional desirable characteristic to the surface. Watts' anti-fouling coating would utilize a mixture of from about 25% to about 90% by weight of the selected coating material and from about 10% to about 75% by weight of the capsaicin constituent.

Mason et al. U.S. Pat. No. 5,290,557 discloses an anti-feedant composition that protects living plants from infestation and feeding by terrestrial molluscs including an active ingredient that comprises a saponin-containing plant extract. When used at a sufficient level this composition is also stated to be fatally toxic to such molluscs. In the discussion of prior art, Mason et al. mention triterpenoid saponins and spirostanol saponins as "identified as compounds effective to kill aquatic molluscs when added to the aquatic environment in which the molluscs live" (see column 1, lines 97–41).

Plummer et al. U.S. Pat. No. 5,240,708 discloses the preparation of an "insect prevention solution" for keeping away spiders and wasps by whipping liquid soap into a foam and combining oil of anise and coriander oil until blended together in the liquid soap, followed by addition and whipping of liquid capsicum until completely blended into the soap, and addition of a major quantity (approximately 90% of the whole composition) of dilute (approximately 5% strength) acetic acid.

K. J. Fischer U.S. Pat. No. 5,226,380 discloses "a protective covering for repelling marine organisms from the exterior of submerged objects comprising a waterproof coating formulated to withstand continual submersion under water; the waterproof coating containing a capsicum derivative material; the capsicum derivative having repellent properties which create a hostile environment for marine organisms in the area of the submerged object to be protected which would otherwise attach themselves to the object to be protected".

Holmes et al. U.S. Pat. No. 5,017,562 at column 6, lines 11–19 acknowledges that saponins have surfactant and detergent properties.

Absent from all the above disclosures is any hint that the disclosed products have the important attribute of durability. There remains a need, therefore, for improved agents with the ability to keep a surface of concern free of occupation, soiling, or damage by unwanted animal life for the useful life of the protected article or at least a significant portion thereof. The importance of durability can be appreciated, for example, by recalling that an anti-fouling paint which needs frequent renewal provides no real advantage over mechanical removal of barnacles as practiced already in the days of sailing ships.

SUMMARY OF THE INVENTION

In accordance with this invention, a non-lethal and environment-friendly bio-repellent composition effective in preventing or minimizing the occupation, damaging, or soiling of various surfaces by unwanted vertebrate animals such as birds, amphibians and rodents and invertebrate animals such as insects, molluscs, and crustaceans comprises a carrier, a bio-repellent amount of capsicum oleoresin, and an amount of a saponin sufficient to enhance the effectiveness of the capsicum oleoresin. Unexpectedly, the bio-repellent effectiveness of the composition of this invention is dramatically greater and longer lasting than that of either capsicum oleoresin or saponin in absence of the other. As a result of the favorable and synergistic interaction of the capsicum oleoresin and saponin components, modest use levels only of the composition art required for effectiveness.

The carrier can comprise water, fatty acid glycerides, emulsions, non-solvent polyureas and other polymeric substances, and pigments in applications such as paints, coatings, cloth, paper, or plastics. When the carrier contains water, the pH of the composition is controlled in the range from 4 to 9.

DESCRIPTION OF THE PREFERRED EMBODIMENTS

The capsicum oleoresin ingredient of the non-lethal bio-repellent composition of this invention is an isolate from plants of the Capsicum family, such as *Capsicum annum* and *Capsicum frutescens*. Available sources of capsicum oleoresin are commonly known as paprika, red pepper chili pepper, and chili powder. Ground red pepper is sometimes referred to as "cayenne", to signify a ground red pepper product of extremely high heat, However, the word "cayenne" does not carry an industry standard of heat level nor is it a particular type of Capsicum. In the spice trade which is the major user of red pepper varietal and origin distinctions are being de-emphasized in favor of standardizing by heat level. Heat levels can be expressed in ASTA (American Spice Trade Association) units equal to parts per million of capsaicin measured by high pressure liquid chromatography, or in organoleptically determined Scoville thermal heat units (SU), whereby 1 ASTA unit=15 SU. Pungency levels of ground red pepper typically range from 300 to 1000 ASTA Heat Units corresponding to 4500 to 60000 SU.

For effectiveness in the composition of this invention, all capsicum preparations containing from 20,000 to 2,000,000 SU of oleoresin capsicum can be used. A tincture of capsicum frutescens (cayenne pepper, active ratio 1/10, alcohol 75% by volume) and oleoresin capsicum obtained by solvent extraction from dried ripe fruit of *Capsicum frutescens L.* or *Capsicum annum L.* standardized to 1,500,000 SU minimum in soybean oil are commercially available.

The saponin ingredient of the non-lethal bio-repellent composition of this invention can be any one or more of the natural saponins which are foam producing water soluble glycosides found widespread in the plant kingdom. Structurally, saponins are characterized by one or more carbohydrate moieties linked to a polycyclic aglycone or sapogenin moiety which can have asteroid, triterpene, or steroid alkaloid ring system. The carbohydrate moieties are most frequently derived from glucose, but saponins in which the aglycone is linked to other saccharides including without limitation rhamnose, xylose, galactose, and mannose, as well as disaccharides and trisaccharides, are also useful. Saponins are usually found in complex mixtures of closely related compounds, but separation of individual saponin compounds from one another is not required for use in accordance with this invention.

Preferred saponins that can be used in accordance with this invention include horse chestnut saponins such as alpha-escin, beta-escin, and combinations thereof; quillaja saponins such as those extracted from the bark of the tree *Ouillaria saponaria*; root saponins such as those extracted from various species of soapwort roots such as Iranian soapwort root (*Acanthophylum squarrosum boiss*, family caryophyllaceae) and Levantine soapwort root (mixture of *Gypsophila paniculata L. G. effusa*, and *G. acutifolia fisch*); saponins extracted from the group of plants consisting of Agave, Dioscorea, Yucca, Medicago, and Cyamopsis, particularly the Yucca species *Yucca mohavenis, Yucca schidigera*, and *Yucca augustifolia*, as well as the saponin source materials of such sapogenins as smilagenin, hecogenin, and tigogenin.

A particularly preferred group of saponins that can be used in accordance with this invention has a triterpene aglycone moiety, especially that of Δ12-oleanene as in quillaic acid (formula I in which R=OH) and gypsogenic acid (formula I in which R=H).

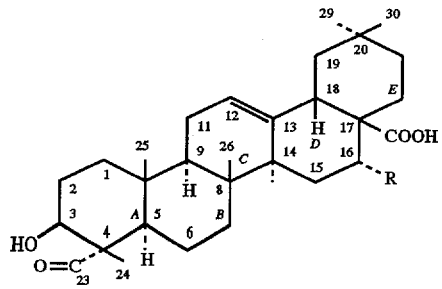

In the composition of this invention, the carrier is the preponderant ingredient, amounting to 85% or more of the whole. The amount of capsicum oleoresin present in the composition of this invention is in the range from 20,000 to 2,000,000 Scoville Units (SU) per 100 grams of the composition, preferably from 30,000 to 300,000 SU, and the amount of saponin (expressed on a dry basis) present in the composition is in the range from 0.02 gram to 10 grams per 100 grams of the composition, preferably from 0.03 gram to 6 grams per 100 grams of the composition.

The relative proportions in the composition of this intention of capsicum oleoresin and saponin to each other are in the range from 2000 SU to 100,000,000 SU of capsicum oleoresin per gram of saponin dry basis, preferably from 10,000 SU to 1,000,000 SU per gram and most preferably from 20,000 SU to 200,000 SU of capsicum oleoresin per gram of saponin dry basis.

The non-lethal bio-repellent composition of this intention can be prepared by combining the ingredients thereof in any order found convenient. It is particularly preferred first to combine the capsicum and saponin ingredients into an emulsion, which affords a stable and useful concentrate for economical storage and shipment for subsequent combination with the carrier to provide the non-lethal bio-repellent composition of this invention.

The preparation of a concentrated emulsion including the capsicum and saponin ingredients of the composition according to this invention proceeds with remarkable ease. Specialized equipment conventionally used for preparing emulsions, exemplified by high speed agitators and colloid mills, can be used but is not necessary. Even hand stirring with a simple paddle is sufficient.

Temperature conditions during the preparation of the non-lethal bio-repellent composition of this invention are not critical and can range from near freezing to just below boiling according to the characteristics of the particular ingredients, from about 5° C. to about 95° C. for compositions containing water. When an ingredient of the composition converts from a solid to a liquid at a temperature within this range, the preparation is preferably carried out above this conversion temperature.

When the carrier ingredient of the non-lethal bio-repellent composition of this invention comprises water, the pH of the composition is preferably in the range from 4 to 9 and can be adjusted at will within this range by the addition of any suitable acid, alkaline, or buffering reagent.

Suitable acid reagents include without limitation hydrochloric acid, sulfuric acid, phosphoric acid, citric acid, propionic acid, and toluenesulfonic acid. Suitable alkaline reagents include without limitation ammonium, potassium, and sodium hydroxides, potassium and sodium bicarbonates and carbonates, t-octylamine and triethanolamine. Suitable buffering reagents include without limitation monosodium and disodium phosphates, tetrapotassium pyrophosphate, borax, potassium acetate, and sodium citrate.

When the carrier ingredient of the non-lethal bio-repellent composition of this invention comprises a fatty acid glyceride, all esters of glycerine with one, two, or three fatty acid residues having 6 to 24 carbon atoms in the fatty acid are effective. Drying as well as non-drying glycerides can be used. Preferred fatty acid glycerides include medium chain length glycerides such as trioctanoin; naturally occurring fats and oils such as castor oil, coconut oil, corn oil, cottonseed oil, fish oil, lard oil, linseed oil, rapeseed oil, soybean oil, and tallow; derivatives of such fats and oils including monoglycerides, diglycerides, acetylated monoglycerides, epoxidized oils and hydrogenated oils; and mixtures of two or more fatty acid glycerides.

When the carrier ingredient of the non-lethal bio-repellent composition of this invention comprises an emulsion, oil-in-water and water-in-oil types can be used. It is a feature of the combination of oleoresin capsicum and saponin according to this invention that it is compatible with all types of emulsifiers such as anionic, cationic, nonionic, and zwitterionic emulsifiers characterized by HLB (hydrophilic-lipophilic balance) values in the range from 4 to 15. In emulsion carriers according to this invention, the non-aqueous phase can be polymeric or non-polymeric. Non-aqueous phase emulsion constituents can include natural and synthetic waxes such as beeswax, carnauba wax, Fischer-Tropsch wax, microcrystalline wax, oxidized polyethylene having an acid number of at least 15, paraffin wax, and sugar cane wax; natural and synthetic rubber latices; and emulsifiable polymers such as homopolymers of vinyl acetate and copolymers thereof with vinylidene chloride, ethylene, diethyl maleate, or dibutyl fumarate, as well as homopolymers and copolymers of acrylic and methacrylic acid esters which can also contain minor amounts of acrylic and methacrylic acids, styrene, and alpha-methylstyrene. A further class of effective emulsion constituents includes graft copolymers of ethylene with polar monomers such as N-vinyl alkylpyrrolidones having 6 to 14 carbon atoms in the alkyl group as disclosed, for example, in Jones U.S. Pat. No. 5,425,955.

When the carrier ingredient of the non-lethal bio-repellent composition of this invention comprises a polymeric substance, addition polymers, condensation polymers, as well as naturally occurring polymers such as cellulose and derivatives thereof such as cellulose acetate-butyrate can be used in such forms as films, fibers, foams, yarns, fabrics, coatings, and molded or extruded plastics. Such polymers preferably have a molecular weight of at least 50000. It is a feature of the combination of oleoresin capsicum and saponin according to this invention that it can be compounded with such polymers by conventional techniques. For example, as much as 6 phr (parts by weight relative to 100 parts by weight of polyvinyl chloride resin) of a concentrated emulsion of oleoresin capsicum and saponin according to this invention can be stirred into a polyvinyl chloride plastisol containing polyvinyl chloride and such conventional additives as plasticizers, stabilizers, and colorants for coating on fabric or molding into articles used in outdoor environments subject to animal traffic. A concentrated emulsion of oleoresin capsicum and saponin according to this invention can also be included in the pad bath used for treatment of textiles and fabrics such as nylon, cotton, or polyester-cotton blends to impart animal repellent effectiveness along with conventional effects such as water repellency, crease resistance and flame retardance.

Additional polymeric substance carriers useful in the non-lethal biorepellent composition of this invention include starch, modified starches, styrene hompolymer and copolymers with acrylonitrile and/or butadiene, non-solvent polyureas, and polyurethane foams and thermoplastics. A particularly preferred class of polymeric substance carriers useful in the non-lethal bio-repellent composition of this invention is the class of acrylic polymers. Such acrylic polymers can be defined as polymers containing a plurality of segments having the formula $$—CH2—CX(COOR')—$$

in which independently at each occurrence X is hydrogen or methyl and R' is hydrogen, an alkyl group having 1 to 10 carbon atoms, a 2-hydroxyethyl group, or a 2-hydroxypropyl group. In particular, such acrylic polymers contain segments derived from the acrylic monomers methyl acrylate, ethyl acrylate, propyl acrylate, isopropyl acrylate, butyl acrylate, isobutyl acrylate, hexyl acrylate, n-octyl acrylate, isooctyl acrylate, nonyl acrylate, isononyl acrylate, n-decyl acrylate, isodecyl acrylate, 2-hydroxyethyl acrylate, 2-hydroxypropyl acrylate, acrylic acid, methyl methacrylate, ethyl methacrylate, propyl methacrylate, isopropyl methacrylate, butyl methacrylate, isobutyl methacrylate, hexyl methacrylate, n-octyl methacrylate, isooctyl methacrylate, 2-ethylhexyl methacrylate, nonyl methacrylate, isononyl methacrylate, n-decyl methacrylate, isodecyl methacrylate, 2-hydroxyethyl methacrylate, 2-hydroxypropyl methacrylate, and methacrylic acid. Within the class of acrylic polymers, copolymers of two, three, or more of the named monomers over a wide range of proportions can readily be prepared by known techniques.

For example, a published procedure describes the preparation of a 50% methyl methacrylate, 49% butyl acrylate, and 1% methacrylic acid terpolymer as an approximately 45% dispersion in water, beginning with the addition to a reactor in the order shown of 30.9 parts of deionized water and 0.1 part of sodium lauryl sulfate, and heating with good agitation under a nitrogen atmosphere to 85° C., followed by the addition of 0.23 parts of ammonium persulfate initiator and then the gradual feeding of a separately prepared monomer emulsion from 19.7 parts of deionized water, 0.1 part sodium lauryl sulfate, 22.5 parts methyl methacrylate, 22.05 parts of butyl acrylate, and 0.45 part of methacrylic acid. The monomer emulsion is fed uniformly over 2.5 hours while maintaining 85° C. After the addition is complete, the temperature is raised to 95° C. to complete the conversion of monomer. The product is then cooled to room temperature, filtered, and packaged.

A large number of representatives of this class of acrylic polymers are commercially available and can be used as carriers in accordance with this invention.

When the carrier ingredient of the non-lethal bio-repellent composition of this invention comprises a pigment, conventional color pigments, extender pigments, and metallic pigments can be used. It is a feature of the non-lethal bio-repellent composition of this invention that full effectiveness is achieved without the need for biologically active pigments such as cuprous oxide, so that any desired color can be obtained by appropriate choice of pigment. Non-limiting examples of pigment types include color pigments such as titanium dioxide, phthalocyanine blue, phthalocyanine green, and yellow and red azo pigments such as Pigment Yellow 180 and Pigment Red 48:1; extender pigments such as calcium carbonate, calcium silicate, and precipitated silicas; and metallic pigments such as bronze and aluminum flakes and powders. A comprehensive disclosure of organic color pigments tabulated by J. Richter in J. Edenbaum (ed) Plastics Additives and Modifiers Handbook (New York: Van Nostrand Reinhold, 1992) at pages 894–898 is here incorporated by reference.

The non-lethal bio-repellent composition of this invention can be incorporated in or applied to many kinds of articles of manufacture and treatments. Non-limiting examples include ship and boat bottom coatings as well as the materials from which such parts of ships and boats are made: ships' holds, subway tunnels, tie down ropes for ships, barges and the like which provide pathways for rodents and insects, garbage and trash containers, animal confinement areas, fixed barriers inside and outside of buildings such as, but not limited to, poultry houses, hog barns, dairy barns, residential, commercial, and industrial buildings exposed and unexposed cables, telephone poles, piping, exterior footings and knee walls of buildings, insulated electrical wiring, plumbing fixtures, and guards used to prevent entry into sewer and water pipes, paper and cloth used in household areas and food storage areas, and all surfaces where the desired protection from unwanted animal occupation, damage, or soiling is desired or required.

Without wishing to be limited by any theory, it is believed that the surprising effectiveness and durability of the non-lethal bio-repellent composition of this invention is due, at least in part, to such unique properties of the emulsion comprising oleoresin capsicum and saponin as a reduction in surface tension within the medium's solid content, which allows the emulsion to efficiently bind to the solids contained in the medium. This molecular binding thereby allows not only a superior distribution of the emulsion but additionally allows for nearly equal and stabilized containment within the entire medium's membrane when said membrane has dried onto the surface to which it has been applied. The reduced surface tension characteristics of the emulsion according to this invention also allow for improved adhesion of the composition to the surface to which it is applied. As a result, and unlike prior art compositions. The repellent effectiveness of the composition of this invention is maintained for long periods of time, up to the durability of the paint film or other system in which it is incorporated.

The following examples are provided by way of illustration and not of limitation of the invention, whose scope is defined by the appended claims.

EXAMPLE 1

A Concentrated Emulsion for Use in Preparing Bio-repellent Compositions According to this Invention An oil-in water emulsion was prepared by stirring together with a simple paint stirrer 84 ounces of oleoresin capsicum concentrate standardized at 1,500,00 Scoville thermal heat units (SU) and 44 ounces of a 50% aqueous concentrate of saponin from quillaja saponaria MOLINA, adding the oleoresin capsicum to the saponin and thus affording one gallon of an amber colored stable emulsion having a pH of approximately 5, surface tension approximately 44.6 dyn/cm, and viscosity greater than that of either ingredient.

This example illustrates the successful preparation of a stable concentrated emulsion for use in preparing bio-repellent compositions according to this invention.

EXAMPLE 2

A Non-lethal Bio-repellent Composition Effective Against Marine Invertebrates

Antifouling coatings for underwater applications to prevent the attachment of marine organisms to treated surfaces were prepared by adding 5 parts by volume of the emulsion of Example 1 to 95 parts by weight of a grey commercial two-part elastomeric acrylic water-based coating (Thiokol FEC-2233 Part A and Part B). Parts A and B were mixed at the rate of 1 part B to 3 parts A, kept for 5 minutes to begin the curing process, then added the emulsion and applied to surfaces within 2 hours or less.

Trials were conducted on 8" by 10" galvanized steel panels, 10" by 12" aluminum panels, wood blocks, and unsaturated polyester plastic sheets. The surfaces were cleaned, primed with a thin layer of Thiokol TPR-415 primer allowed to dry for about 5 minutes, then treated with a single coat of Part A at the rate of 8–10 dry mils and allowed to cure for about 3 hours, and finally with the two part system containing the emulsion of Example 1 at the rate of 20 dry mils.

When immersed in sea water at 78° F., there was no sign of any crustacean or barnacle adherence for at least three months to surfaces treated with the elastomeric acrylic coating containing the emulsion of this invention. Identical surfaces similarly treated with the elastomeric acrylic water-based coating without the emulsion of Example 1 (a no-add control), or left entirely untreated, that were exposed at the same time attached a number of crustaceans and barnacles.

The results of these trials demonstrate the surprising synergistic effect of the composition of this invention in providing full protection under the conditions of the trials while the no-add control and untreated compositions were completely ineffective.

EXAMPLE 3

A Non-lethal Bio-repellent Composition Effective Against Birds and Insects

The emulsion of Example 1 was incorporated at a load level of 5% by volume into a flexible elastomeric acrylic water based thermal barrier coating formulated with borosilicate ceramic particles as well as nonmetallic fungicide and mildewcide (Ceramicoat K-21 Flex/Guard Domestic, EERS International Inc. Fort Lauderdale Fla. 33306). So treated coatings, and untreated coatings for comparison were applied at a rate of 1 gallon per 100 square feet or 9.4 dry mils to metal roof structures, commercial fish tank side walls, coated electrical cables, and trash containers. All the treated surfaces remained free of fowl residue and evidence of insect activity observed on surfaces receiving the acrylic coating without the emulsion of Example 1.

These results demonstrate the effectiveness of a composition of this invention in protecting against occupation, damage, and soiling by birds and insects.

EXAMPLE 4

A Non-lethal Bio-repellent Composition Effective Against Fire Ants

The emulsion of Example 1 was incorporated at a load level of 5% by volume into a white exterior elastomeric acrylic water based coating (Ceramicoat Agricultural, EERS International Inc.) which was then applied around the base of young citrus trees where there had been previous problems with fire ants killing some of the young trees. A band of approximately 18 inches was covered to a thickness of 3-4 dry mils on each tree. It was observed that after application there was no longer evidence of fire ant activity on the trees, and there were no other insects observed that would ordinarily use the tree's trunk as a pathway.

These results demonstrate the effectiveness of a composition of this invention in protecting against occupation and damage by fire ants.

EXAMPLE 5

The emulsion of Example 1 was incorporated at a load level of 5% by volume into canola oil, and the canola oil containing the emulsion was applied in the Great Lakes area (fresh water) to boat docks, dock pilings, and diving platforms in areas where ducks and sea gulls were accustomed to land and leave droppings. After application there was no evidence of this problem for an entire summer season (four months), while untreated boats and dock areas were heavily fouled.

It was also observed that it was sufficient to apply the canola oil containing the emulsion on approximately six inches of the outer edge of the dock on both sides to obtain the desired results.

Photographs taken at the scene four months after treatment of the area clearly show the difference between the clean treated areas and soiled areas on untreated boats and dock areas. Thus the results demonstrate the effectiveness of a composition of this invention in protecting against occupation and soiling by ducks.

EXAMPLE 6

For the control of tree frogs which have a tendency to congregate on window sills and and there defecate and also leave a mucous deposit, the composition of emulsion and canola oil of Example 5 was applied to residential window sills by ordinary paint brush so that the surface was completely covered. The surface was the metal frame and sill of a 36"×40" window, crank out type, and it was noted that after application of the composition there was no evidence of fouling, defecation or mucous residue, with weekly observations, for a period of four months.

Additionally, trials were conducted on the same size and type of windows on the same side of the same building, all previously having experienced the same tree frog problem, with each of the individual components containing the emulsion, namely—canola oil only, oleoresin capsicum of 1,500,000 Scoville units strength, and triterpene saponin 50% applied at the same rate, by ordinary paint brush, covering the metal frames and sill surfaces so that a complete covering was achieved.

The following observations were made:

a) The triterpene saponin 50% had no effect whatsoever in that defecation and mucous residue evidence of the tree frogs was observed in the first 24 hours after application.
b) Canola oil—same results as (a) above.
c) Oleoresin capsicum 1,500,000 SU—there was no evidence of the tree frogs for a period of two weeks. However, after two weeks there appeared some evidence of tree frog presence, defecation, although limited. Further it was observed that after three weeks an increased amount of evidence was observed, defecation and mucous residue, indicating that it was no longer effective.

These results demonstrate the unexpected and dramatic effectiveness of a composition of this invention in durably protecting against occupation and soiling by tree frogs.

We claim:

1. A non-lethal bio-repellent composition comprising a carrier, a bio-repellent amount of capsicum oleoresin, and an amount of a saponin sufficient to enhance the effectiveness of the capsicum oleoresin, said capsicum oleoresin approximates 10,000 SU to 1,000,000 SU per gram of saponin, said saponin containing at least one carbohydrate moiety and at least one aglycone moiety selected from the group consisting of triterpene, steroids, and alkaloids; wherein the bio-repellent effectiveness of said composition being greater than that of either capsicum oleoresin in absence of saponin or saponin in absence of capsicum oleoresin.

2. A composition according to claim 1, in which the carrier comprises water.

3. A composition according to claim 2, comprising an oil-in-water emulsion.

4. A composition according to claim 1, in which the carrier comprises a fatty acid glyceride.

5. A composition according to claim 1, in which the carrier comprises a polymeric substance having a molecular weight of at least 50,000.

6. A composition according to claim 2, in which the pH is in the range of 4 to 9.

7. A composition according to claim 4, in which the fatty acid glyceride is a fatty oil liquid at 25° C.

8. A composition according to claim 5, in which the polymeric substance includes a plurality of segments having the formula

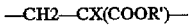

—CH2—CX(COOR')— in which independently at each occurrence X is hydrogen or methyl and R' is hydrogen, an alkyl having 1 to 1-carbon atoms, a 2-hydroxyethyl group, or a 2-hydroxypropyl group.

9. A composition according to claim 5, additionally including a pigment.

10. A composition according to claim 1, in which the saponin contains at least one carbohydrate moiety and at least one aglycone moiety selected from the group consisting of triterpene, steroids, and alkaloids.

11. A composition according to claim 1, in which the aglycone moiety is a triterpene.

12. A composition according to claim 11, in which the aglycone moiety includes a Δ12-Oleanene.

13. A composition according to claim 12, in which the aglycone moiety is represented by the formula

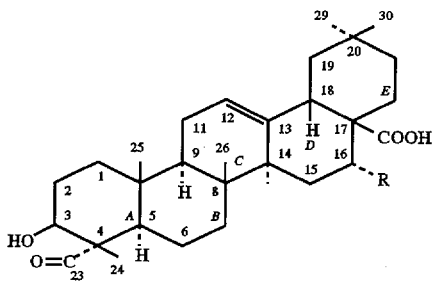

in which R is selected from the group consisting of hydrogen and hydroxyl.

14. A method of inhibiting the occupation, damaging, or soiling of a surface by unwanted vertebrate or invertebrate animal life, which comprises the application to said surface of a composition according to claim 1.

15. A method according to claim 14, in which the inhibiting effect persists for at least three months.

16. An article of manufacture having a surface with diminished tendency to be occupied, damaged, or soiled by unwanted vertebrate or invertebrate animal life and having applied to said surface a composition according to claim 1.

17. An article according to claim 16, in which said surface is immersed in water.

18. An article according to claim 16, in which said surface is part of a structure on land below ground level.

19. An article according to claim 16, in which said surface is part of a structure on land above ground level.

20. A stable emulsion comprising water, capsicum oleoresin, and a saponin, in which the relative proportions of capsicum oleoresin and saponin are in the range of 10,000 SU to 1,000,000 SU of capsicum oleoresin per gram of saponin dry basis.

21. The method of preparing a non-lethal bio-repellent composition comprising a carrier, a bio-repellent amount of capsicum oleoresin, and an amount of a saponin sufficient to enhance the effectiveness of the capsicum oleoresin, the bio-repellent effectiveness of said composition being greater than that of either capsicum oleoresin in absence of saponin or saponin in absence of capsicum which comprises the combination of a stable emulsion according to claim 20 with a carrier.

* * * * *

UNITED STATES PATENT AND TRADEMARK OFFICE
CERTIFICATE OF CORRECTION

PATENT NO.   : 5,698,191
DATED        : Dec. 16, 1997
INVENTOR(S)  : Charles Weirsma, et al It is certified that error appears in the above-indentified patent and that said Letters Patent is hereby corrected as shown below:

In the claims:

In claim 8, at column 10, line 54, before "carbon", delete "1-" and insert therefore --10--.

Signed and Sealed this

Fourth Day of August, 1998

*Attest:*

*Attesting Officer*

BRUCE LEHMAN

*Commissioner of Patents and Trademarks*